United States Patent
Hotta et al.

(10) Patent No.: US 7,235,222 B2
(45) Date of Patent: Jun. 26, 2007

(54) PROCESS FOR TREATING WASTE ANESTHETIC GAS

(75) Inventors: Masatoshi Hotta, Kanagawa (JP); Masakazu Oka, Kanagawa (JP); Yoshio Furuse, Kanagawa (JP); Hitoshi Atobe, Kanagawa (JP); Shigehiro Chaen, Kanagawa (JP)

(73) Assignee: Showa Denko K.K., Tokyo (JP)

( * ) Notice: Subject to any disclaimer, the term of this patent is extended or adjusted under 35 U.S.C. 154(b) by 167 days.

(21) Appl. No.: 10/381,422

(22) PCT Filed: Sep. 27, 2001

(86) PCT No.: PCT/JP01/08441

§ 371 (c)(1),
(2), (4) Date: Mar. 25, 2003

(87) PCT Pub. No.: WO02/26355

PCT Pub. Date: Apr. 4, 2002

(65) Prior Publication Data

US 2003/0185735 A1    Oct. 2, 2003

Related U.S. Application Data

(60) Provisional application No. 60/241,743, filed on Oct. 20, 2000.

(30) Foreign Application Priority Data

Sep. 27, 2000 (JP) ............................. 2000-294794
May 15, 2001 (JP) ............................. 2001-144201

(51) Int. Cl.
  A61M 16/00 (2006.01)
  B01D 46/00 (2006.01)
  B01J 8/00 (2006.01)
  C01B 21/00 (2006.01)

(52) U.S. Cl. .................... 423/235; 95/17; 128/200.24; 128/203.25; 423/239.1; 423/239.2

(58) Field of Classification Search ................ 423/235, 423/239.1, 239.2; 128/203.25, 200.24; 95/17
See application file for complete search history.

(56) References Cited

U.S. PATENT DOCUMENTS

| 5,171,553 A | 12/1992 | Li et al. |
| 5,231,980 A | 8/1993 | Filipovic et al. |
| 6,347,627 B1 * | 2/2002 | Frankie et al. ......... 128/201.21 |
| 6,405,539 B1 * | 6/2002 | Stach et al. ................... 62/3.4 |

FOREIGN PATENT DOCUMENTS

| DE | 41 25 538 A | 2/1992 |
| DE | 42 08 521 A | 9/1993 |
| DE | 43 08 940 A | 9/1994 |
| EP | 0 284 227 | 9/1988 |
| JP | 61-45486 B | 10/1986 |
| JP | 61-45487 B | 10/1986 |
| JP | 63-315127 | 12/1988 |
| JP | 10-165818 | 6/1998 |
| WO | WO 00 23176 A | 4/2000 |

OTHER PUBLICATIONS

Rinsho Masui (Clinical Anesthesia) vol. 1, No. 1, p. 98 (1977).
Fujita Gakuen Igaku-Kai Shi (Journal of Medical Society of Fujita Educational Institute) vol. 5, p. 117 (1981).
Masui (Anesthesia) No. 28, p. 1242 (1979).
International Search Report for PCT/JP01/08441 dated Jun. 27, 2002.

* cited by examiner

*Primary Examiner*—Edward M. Johnson
(74) *Attorney, Agent, or Firm*—Sughrue Mion, PLLC

(57) ABSTRACT

To provide a process and an apparatus for treating a waste anesthetic gas containing a volatile anesthetic and nitrous oxide discharged from an operating room by introducing the gas into an adsorbing cylinder filled with an adsorbent, where the volatile anesthetic contained in the waste anesthetic gas is adsorbed and thereby removed, and successively introducing the gas into a catalyst layer filled with a nitrous oxide decomposition catalyst, where nitrous oxide is decomposed into nitrogen and oxygen. By using the process and the apparatus for treating a waste anesthetic gas of the present invention, a volatile anesthetic having a possibility of destroying the ozone layer or nitrous oxide as a global warming gas can be made harmless while preventing the release into atmosphere.

21 Claims, 4 Drawing Sheets

PROCESS FOR TREATING WASTE ANESTHETIC GAS

CROSS REFERENCE TO RELATED APPLICATIONS

This application is an application filed under 35 U.S.C. §111(a) claiming benefit pursuant to 35 U.S.C. §119(e)(1) of the filing dates of U.S. Provisional Application No. 60/241,743 filed Oct. 20, 2000 pursuant to 35 U.S.C. §111(b).

TECHNICAL FIELD TO WHICH THE INVENTION BELONGS

The present invention relates to a process and an apparatus for treating a waste anesthetic gas containing a volatile anesthetic and nitrous oxide discharged from an operating room.

BACKGROUND ART

Since 1960, contamination of an operating room by anesthetic gas and adverse effect of the anesthetic gas on the health of workers in the operating room have been taken as a matter of issue. It is known that as a result of long term inhalation of the anesthetic gas leaked in the operating room, the health is disordered. The anesthetic gas means a mixed gas containing nitrous oxide, a volatile anesthetic and oxygen, and the waste anesthetic gas means anesthetic gas after the respiration of a patient. The composition of the waste anesthetic gas is approximated to the composition of the anesthetic gas and contains a volatile anesthetic, nitrous oxide of high concentration, and oxygen. In the U.S.A., the National Institute of Occupational Safety and Health (NIOSH) recommends to reduce, as a permissible standard, nitrous oxide ($N_2O$) to 25 ppm or less and a volatile anesthetic to 2 ppm in the case of a sole use and to 0.5 ppm or less in the case of a combination use with nitrous oxide. Accordingly, all anesthesia machines are obliged to be equipped with a waste anesthetic gas removing apparatus and at the present time, the environment in the operating room can reach the above-described levels.

The waste anesthetic gas removing apparatus is an apparatus for discharging the waste anesthetic gas outdoors from the exhalation of a patient by letting a compression air or the like to accompany the gas. However, the gas discharged from each operating room by the waste anesthetic gas removing apparatus is released into atmosphere without passing through any treatment at the present time.

The waste anesthetic gas discharged from an operating room differs from the nitrous oxide-containing exhaust gas discharged from factories or incineration facilities in the following two points:

(1) the concentration of the nitrous oxide contained in the waste anesthetic gas is very high and from 3 to 70%, and (2) the waste anesthetic gas contains a volatile anesthetic gas.

Among volatile anesthetics, volatile anesthetics containing chlorine are said to destroy the ozone layer. Also, in the third session of the Conference of the parties (COP3), nitrous oxide is, as well as nitrogen dioxide, methane and chlorofluorocarbon, particularly taken notice of as a global pollutant which brings about elevation of temperature due to greenhouse effect (the warming effect is as high as about 300 times the carbon dioxide).

Accordingly, from the standpoint of global environment protection, the waste anesthetic gas should not be released into atmosphere as it is using the waste anesthetic gas removing apparatus but both volatile anesthetic and nitrous oxide contained in the waste anesthetic gas must be removed or rendered harmless.

With respect to conventional methods for treating the waste anesthetic gas, (1) a method of decomposing the nitrous oxide contained in the waste anesthetic gas is described in JP-B-61-45486 (the term "JP-B" as used herein means an "examined Japanese patent publication"), JP-B-61-45487, U.S. Pat. No. 4,259,303 (JP-B-61-50650 and JP-B-62-27844). Also, (2) a method of cooling and thereby removing volatile anesthetics contained in the waste anesthetic gas is proposed by Arai et al (see, *Rinsho Masui (Clinical Anesthesia)*, Vol. 1, No. 1, page 98 (1977), *Fujita Gakuen Igaku-kai Shi(Journal of Medical Society of Fujita Educational Institute)*, Vol. 5, page 117 (1981)). Furthermore, (3) a method of thermally decomposing the nitrous oxide by a Nichrome wire heating is reported as a method of treating nitrous oxide contained in the waste anesthetic gas without using a catalyst (see, *Masui(Anesthesia)*, No. 28, page 1242 (1979)).

According to the method (1) of decomposing nitrous oxide, nitrous oxide in a high concentration may be decomposed but nitrogen monoxide (NO) and nitrogen dioxide ($NO_2$) (hereinafter collectively referred to as "NOx") as nitrogen oxides are produced in an amount of 5 to 32 ppm, thus, generation of NOx in excess of the allowable concentration of 3 ppm (TWA, time weighted average) for $NO_2$ remains as a problem. In addition, when moisture in an amount of, for example, approximately from 1 to 3% is present in the reaction gas, the catalyst may decrease in the activity, and this remains as a problem to be solved.

When a waste anesthetic gas is fed as it is to a nitrous oxide decomposition catalyst, decrease in the specific surface area of the nitrous oxide decomposition catalyst is incurred in some cases to cause extreme reduction of the activity. The reasons therefor is not clearly known but it is presumed that acids generated at the decomposition of the volatile anesthetic deactivate the nitrous oxide decomposition catalyst. Accordingly, in order to maintain the activity of the nitrous oxide decomposition catalyst, volatile anesthetic must be removed, however, a method for effectively removing volatile anesthetic contained in the waste anesthetic gas is heretofore not known.

The above method (2) of cooling and thereby removing volatile anesthetic contained in the waste anesthetic gas proposed by Arai et al has a problem in the profitability because a volatile anesthetic gas removing device and a cooling unit for cooling the removing device must be installed in each operating room. In addition, the installation of a large apparatus such as cryogenic refrigeration unit in an operating room is not preferred from the location and hygienic aspects. Furthermore, in the case of treating a large amount gas flown from the pipeline to which the waste anesthetic gases discharged from respective operating rooms are converged, there arises a problem that the volatile anesthetic cannot be satisfactorily removed. From these reasons, this method is not used in practice.

The above method (3) of thermally decomposing nitrous oxide by the Nichrome wire heating without using a catalyst is not preferred for the use in hospitals in view of safety, because the reaction temperature is as high as 900° C., a neutralization cleaning unit is necessary, and the concentration of NOx generated is very high and around 0.1%.

A process and an apparatus capable of continuously treating volatile anesthetic and nitrous oxide contained in a relatively large amount in the waste anesthetic gas discharged from each operating room have heretofore not been known. To keep up with the current increase in concern for the global warming due to nitrous oxide, development of a process and an apparatus capable of continuously treating a waste anesthetic gas containing volatile anesthetic gas and nitrous oxide is being demanded.

The present invention made under these circumstances is to provide a process and an apparatus for treating a waste anesthetic gas containing a volatile anesthetic and nitrous oxide discharged from an operating room.

SUMMARY OF THE INVENTION

As a result of extensive investigations to solve the above-described problems, the present inventors have found that these problems can be overcome by using a process for treating a waste anesthetic gas, comprising (1) a step of introducing a waste anesthetic gas containing a volatile anesthetic and nitrous oxide into, for example, at least one of adsorbing cylinders connected in parallel, and contacting the gas with an adsorbent filled in the adsorbing cylinder, thereby adsorption-removing the volatile anesthetic contained in the waste anesthetic gas, and (2) a step of contacting the gas containing nitrous oxide discharged from the step (1) with a catalyst, thereby decomposing the nitrous oxide; and further by using an apparatus comprising an adsorbing cylinder filled with an adsorbent for adsorbing a volatile anesthetic, a decompression unit for desorbing the adsorbed volatile anesthetic from the adsorbent and regenerating the adsorbent, a cooler for cooling or freezing the desorbed volatile anesthetic, a recovery unit for recovering the cooled or frozen volatile anesthetic, and a decomposition reactor filled with a catalyst for decomposing the nitrous oxide contained in the waste anesthetic gas. The present invention has been accomplished based on this finding.

DISCLOSURE OF THE INVENTION

The present invention relates to the following matters 1 to 31.

1. A process for treating a waste anesthetic gas containing a volatile anesthetic and nitrous oxide discharged from an operating room comprising steps of contacting the gas with an adsorbent, thereby adsorption-removing the volatile anesthetic contained in the waste anesthetic gas, and then contacting the gas containing nitrous oxide with a catalyst for decomposing the nitrous oxide, thereby decomposing the nitrous oxide.

2. The process for treating a waste anesthetic gas as described in 1 above, wherein the treating comprises the following two steps:

(1) a step of introducing a waste anesthetic gas containing a volatile anesthetic and nitrous oxide discharged from an operating room into an adsorbing cylinder, and contacting the gas with an adsorbent filled in the adsorbing cylinder, thereby adsorption-removing the volatile anesthetic contained in the waste anesthetic gas, and (2) a step of contacting the gas containing nitrous oxide discharged from the step (1) with a catalyst, thereby decomposing the nitrous oxide.

3. The process for treating a waste anesthetic gas as described in 1 above, wherein the treating comprises the following two steps:

(1) a step of introducing a waste anesthetic gas containing a volatile anesthetic and nitrous oxide discharged from an operating room into at least one of adsorbing cylinders connected in parallel, and contacting the gas with an adsorbent filled in the adsorbing cylinder, thereby adsorption-removing the volatile anesthetic contained in the waste anesthetic gas, and (2) a step of contacting the gas containing nitrous oxide discharged from the step (1) with a catalyst, thereby decomposing the nitrous oxide.

4. The process for treating a waste anesthetic gas as described in 2 or 3 above, further comprising the following step (3):

(3) a step of desorbing the volatile anesthetic from the adsorbent having adsorbed the volatile anesthetic to regenerate the adsorbent, cooling the desorbed volatile anesthetic, and recovering the liquefied or frozen volatile anesthetic.

5. The process for treating a waste anesthetic gas as described in 4 above, wherein the step (1) and the step (3) are performed at the same time by changing over the adsorbing cylinders connected in parallel alternately to the step (1) and to the step (3).

6. The process for treating a waste anesthetic gas as described in 5 above, wherein the changeover between the step (1) and the step (3) is performed under control by a sequencer.

7. The process for treating a waste anesthetic gas as described in 4 above, wherein the step (3) is performed under reduced pressure and the gas discharged from the step (3) is introduced into at least one of adsorbing cylinders connected in parallel and contacted with an adsorbent filled in the adsorbing cylinders to remove by adsorption the unrecovered volatile anesthetic contained in the gas discharged from the step (3).

8. The process for treating a waste anesthetic gas as described in 4 above, wherein the step (3) is performed under reduced pressure while introducing a purge gas and the gas discharged from the step (3) is introduced into at least one of adsorbing cylinders connected in parallel and contacted with an adsorbent filled in the adsorbing cylinder to remove by adsorption the unrecovered volatile anesthetic contained in the gas containing a purge gas discharged from the step (3).

9. The process for treating a waste anesthetic gas as described in 4 above, wherein in the step (3), the temperature at the cooling of the desorbed volatile anesthetic is from −95 to 10° C.

10. The process for treating a waste anesthetic gas as described in 1 above, wherein the concentration of the volatile anesthetic contained in the waste anesthetic gas is from 0.1 to 3%.

11. The process for treating a waste anesthetic gas as described in 1 above, wherein the volatile anesthetic is a fluoroether compound.

12. The process for treating a waste anesthetic gas as described in 1 above, wherein the volatile anesthetic is 2-bromo-2-chloro-1,1,1-trifluoroethane, 1-chloro-2,2,2-trifluoroethyl difluoromethyl ether and/or fluoromethyl-2,2,2-trifluoro-1-(trifluoromethyl) ethyl ether.

13. The process for treating a waste anesthetic gas as described in 1 above, wherein the adsorbent is at least one adsorbent selected from the group consisting of activated carbon, zeolite, silica, mesoporous silica and alumina.

14. The process for treating a waste anesthetic gas as described in 13 above, wherein the adsorbent has a pore size of 5 to 100 Å.

15. The process for treating a waste anesthetic gas as described in 1 above, wherein the concentration of the nitrous oxide contained in the waste anesthetic gas is from 3 to 70%.

16. The process for treating a waste anesthetic gas as described in 1 above, wherein the catalyst for decomposing the nitrous oxide is an alumina-type catalyst.

17. The process for treating a waste anesthetic gas as described in 1 above, wherein the catalyst for decomposing the nitrous oxide is at least one catalyst selected from the group consisting of the following catalysts (I) to (III):

(I) a catalyst comprising a support having supported thereon aluminum, magnesium and rhodium, (II) a catalyst comprising an alumina support having supported thereon magnesium and rhodium, and (III) a catalyst comprising a support having supported thereon rhodium, the support having therein a spinel crystalline complex oxide formed by magnesium and at least a part of aluminum.

18. The process for treating a waste anesthetic gas as described in 1 above, wherein the catalyst for decomposing the nitrous oxide is at least one catalyst selected from the group consisting of the following catalysts (IV) to (VI):

(IV) a catalyst comprising a support having supported thereon aluminum, rhodium and at least one metal selected from the group of zinc, iron and manganese.

(V) a catalyst comprising an alumina support having supported thereon rhodium and at least one metal selected from the group of zinc, iron and manganese.

(VI) a catalyst comprising a support having supported thereon rhodium, the support having therein a spinel crystalline complex oxide formed by at least a part of aluminum and at least one metal selected from the group of zinc, iron and manganese.

19. The process for treating a waste anesthetic gas as described in 1 above, wherein the temperature at the decomposition of the nitrous oxide is from 200 to 600° C.

20. The process for treating a waste anesthetic gas as described in any one of 17 to 19 above, wherein the amount of NOx generated at the decomposition of the nitrous oxide is 1 ppm or less.

21. The process for treating a waste anesthetic gas as described in 2 or 3 above, wherein in the step (2), heat exchange is performed between the gas discharged from the step (1) and the gas discharged from the step (2) after the decomposition of the nitrous oxide.

22. The process for treating a waste anesthetic gas as described in 19 above, wherein the concentration of the nitrous oxide contained after the decomposition of the nitrous oxide is detected and the temperature at the decomposition of the nitrous oxide is controlled based on the detected concentration of nitrous oxide.

23. An apparatus for treating a waste anesthetic gas containing a volatile anesthetic and nitrous oxide discharged from an operating room, the apparatus comprising an adsorbing cylinder filled with an adsorbent for adsorbing a volatile anesthetic, a decompression unit for desorbing the adsorbed volatile anesthetic from the adsorbent and regenerating the adsorbent, a cooler for cooling or freezing the desorbed volatile anesthetic, a recovery unit for recovering the cooled or frozen volatile anesthetic, and a decomposition reactor filled with a catalyst for decomposing the nitrous oxide contained in the waste anesthetic gas.

24. The apparatus for treating a waste anesthetic gas as described in 23 above, wherein the adsorbing cylinder is connected with the decomposition reactor such that a waste anesthetic gas containing a volatile anesthetic and nitrous oxide is introduced into the adsorbing cylinder filled with an adsorbent and then the gas containing nitrous oxide discharged from the adsorbing cylinder is introduced into the decomposition reactor filled with a catalyst for decomposing the nitrous oxide.

25. The apparatus for treating a waste anesthetic gas as described in 23 above, wherein a plurality of adsorbing cylinders are provided and the adsorbing cylinders are connected in parallel.

26. The apparatus for treating a waste anesthetic gas as described in 23 above, which comprises a line for returning the gas to the inlet of an adsorbing cylinder after the volatile anesthetic desorbed from the adsorbent is cooled and the liquefied or frozen volatile anesthetic is recovered.

27. The apparatus for treating a waste anesthetic gas as described in 23 above, which comprises a purge gas-introducing line connected so as to introduce a purge gas into an adsorbing cylinder and a line for returning the gas containing the purge gas to the inlet of an adsorbing cylinder after the volatile anesthetic desorbed from the adsorbent is cooled and the liquefied or frozen volatile anesthetic is recovered.

28. The apparatus for treating a waste anesthetic gas as described in 23 above, which comprises a pump for inducing a diluting gas capable of diluting the gas introduced into the decomposition reactor and a line for introducing the diluting gas into the inlet of the decomposition reactor.

29. The apparatus for treating a waste anesthetic gas as described in 23 above, which comprises a heat exchanger for performing heat exchange between the gas introduced into the decomposition reactor and the gas discharged from the decomposition reactor.

30. The apparatus for treating a waste anesthetic gas as described in 29 above, wherein the decomposition reactor and the heat exchanger are integrally constructed and the heat exchange between the gas introduced into the decomposition reactor and the gas discharged from the decomposition reactor is performed in the heat exchanger.

31. The apparatus for treating a waste anesthetic gas as described in 23 above, which comprises a nitrous oxide gas detector for detecting the concentration of the nitrous oxide contained in the gas discharged from the decomposition reactor and a temperature controlling unit for controlling the temperature of the decomposition reactor based on the nitrous oxide concentration measured by the nitrous oxide gas detector.

MODE FOR CARRYING OUT THE INVENTION

Figure 1:
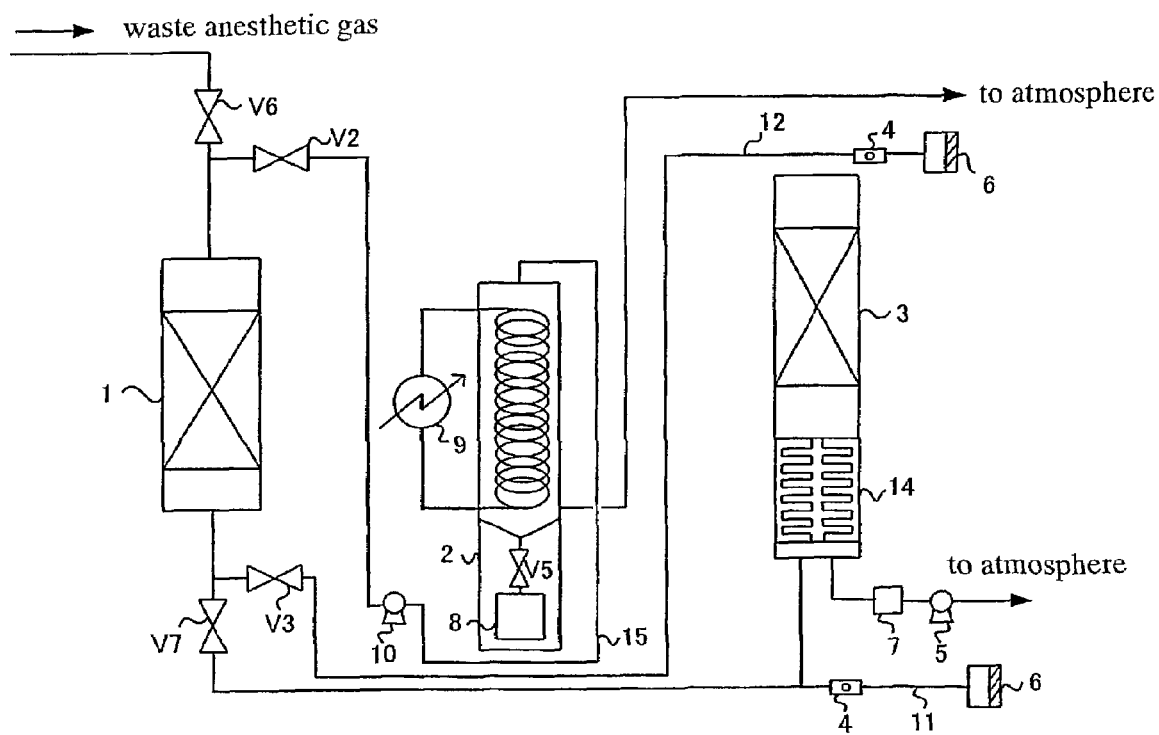
FIG. 1 is a schematic view showing one example of the apparatus for treating a waste anesthetic gas of the present invention.

The present invention is described in detail below.

The process for treating a waste anesthetic gas containing a volatile anesthetic and nitrous oxide of the present invention is described below.

The process for treating a waste anesthetic gas of the present invention is characterized in steps of contacting a waste anesthetic gas containing a volatile anesthetic and nitrous oxide with an adsorbent and contacting the gas with a catalyst for decomposing the nitrous oxide.

The process for treating a waste anesthetic gas of the present invention is characterized in that a step (1) of introducing a waste anesthetic gas containing a volatile anesthetic and nitrous oxide into an adsorbing cylinder and contacting the gas with an adsorbent filled in said adsorbing cylinder, thereby adsorption-removing the volatile anesthetic contained in the waste anesthetic gas is first performed, and then, a step (2) of introducing the gas containing nitrous oxide discharged from the step (1) into the decomposition reactor filled with a catalyst for decomposing the nitrous oxide, and contacting the nitrous oxide with a catalyst, thereby decomposing the nitrous oxide to nitrogen and oxygen, is performed.

The process for treating a waste anesthetic gas of the present invention is furthermore characterized in the following steps:

a step (1) of introducing a waste anesthetic gas containing a volatile anesthetic and nitrous oxide into at least one of adsorbent cylinders connected in parallel which can be operated by changing over them and contacting the gas with an adsorbent filled in said adsorbing cylinder, thereby adsorption-removing the volatile anesthetic contained in the waste anesthetic gas is first performed, and then, a step (2) of introducing the gas containing nitrous oxide discharged from the step (1) into the decomposition reactor filled with a catalyst for decomposing the nitrous oxide, and contacting the nitrous oxide with a catalyst, thereby decomposing the nitrous oxide to nitrogen and oxygen, is performed.

For the volatile anesthetic mixed with nitrous oxide, halothane (2-bromo-2-chloro-1,1,1-trifluoroethane) has been heretofore used, however, in recent years, fluoroethers such as isoflurane (1-chloro-2,2,2-trifluoroethyl difluoromethyl ether), sevoflurane (fluoromethyl 2,2,2-trifluoro-1-(trifluoromethyl)ethyl ether), enflurane (2-chloro-1,1,2-trifluoroethyl difluoromethyl ether) and desflurane (1,2,2,2-tetrafluoroethyl difluoromethyl ether) are predominantly used. These fluoroether-type volatile anesthetics are used, for example, after feeding oxygen to an anesthesia machine filled with a fluoroether-type volatile anesthetic to have a content of from 2 to 3% in an anesthetic gas and mixing a vapor pressure portion of the fluoroether-type volatile anesthetic with nitrous oxide.

Respective components are contained in the anesthetic gas for use in an operating room, for example, in such amounts that nitrous oxide is 4 L/min, oxygen is 2 L/min and volatile anesthetic is from 2 to 3% of the entire anesthetic gas. The volatile anesthetic is from 0.1 to 3% of the waste anesthetic gas after it was used as anesthetic gas. For example, assuming that volatile anesthetic is 3% of the waste anesthetic gas and once operation takes 8 hours, in the case of using sevoflurane as a volatile anesthetic, the amount of the volatile anesthetic used is about 90 L for the gas form and about 771 g for the liquid form, per one operating room. For removing this sevoflurane only by adsorption to activated carbon, the activated carbon, for example, coconut shell husk carbon Y-10 (produced by Ajinomoto Fine Techno Corp.) is used in an amount of about 9.3 kg according to the experiment by the present inventors.

The waste anesthetic gas discharged from an operating room is released out of a hospital through a pipeline converging respective operating rooms in many cases. When operations are performed at the same time or an operation takes a long time, activated carbon must be used in a very large amount as many times as the above-described amount and for exchanging the activated carbon every each operation, a great deal of time and labors are necessary and a huge cost disadvantageously results.

In the process for treating a waste anesthetic gas of the present invention, it is possible to adsorb the volatile anesthetic contained in the waste anesthetic gas using one adsorbing cylinder. However, in order to treat a waste anesthetic gas continuously and efficiently, it is desirable from the above reasons to use more than one adsorbing cylinders, and to connect the more than one adsorbing cylinders in parallel.

More than one adsorbing cylinders connected in parallel can be operated by periodically changing over them during the working. The size of the adsorbing cylinder and the amount of the adsorbent filled in the adsorbing cylinder can be appropriately selected depending on the flow rate of the waste anesthetic gas and the concentration of the volatile anesthetic, such that the volatile anesthetic does not flow out from the adsorbing cylinder outlet. In order to efficiently perform the adsorption of the volatile anesthetic, the adsorbing cylinders are preferably operated by changing the gas flow to a new adsorbing cylinder at the time when the adsorption by the adsorbent reaches about ¾ of the adsorption capacity, whereby the adsorbing operation can be conducted continuously.

Examples of the adsorbent which can be used in the process for treating a waste anesthetic gas of the present invention include zeolite, silica, mesoporous silica, alumina and activated carbon. At least one adsorbent selected from these adsorbents can be used and particularly, activated carbon or alumina is preferred. In case of activated carbon, activated carbon containing little amount of ash is preferable. The content of ash may be preferably 1% by mass or less, more preferably 0.5% by mass or less, and most preferably 0.2% by mass or less. Ash means inorganic components contained in activated carbon such as $SiO_2$, $Al_2O_3$, $Fe_2O_3$, CaO, MgO, $K_2O$, $Na_2O$, $TiO_2$ and $Cr_2O_3$. Among these inorganic components, less content of alkali metal and alkali earth metal compound is preferable. If the adsorption and desorption treatment of the volatile anesthetic is repeated by using activated carbon containing much alkali metals and/or alkali earth metals, it may lead to decomposition of the volatile anesthetic. In case of adsorbents other than activated carbon, less content of alkali metal and alkali earth metal compound is similarly preferable. It may be preferably less than 300 ppm, more preferably less than 100 ppm, and further more preferably less than 50 ppm. In view of the molecular size of the volatile anesthetic, the adsorbent preferably has a pore size of 5 to 100 Å, preferably from 7 to 50 Å, more preferably from 7 to 20 Å. In the case of activated carbon, the activated carbon which has a pore size of more than 100 Å may be used as an adsorbent.

In the case where the waste anesthetic gas contains moisture, the waste anesthetic gas before the adsorption treatment may be cooled or contacted with an adsorbent such as silica and hydrophilic zeolite to remove the moisture.

An adsorbent selected from the above-described adsorbents may be used alone, or two or more thereof may be used in combination at an arbitrary ratio. The ratio of mixing two or more adsorbents may be appropriately selected according to conditions such as the concentration the waste anesthetic gas.

After the waste anesthetic gas is contacted with an adsorbent and thereby the volatile anesthetic is adsorption-removed therefrom, the resulting gas containing nitrous oxide is decomposed into nitrogen and oxygen using a catalyst for decomposing the nitrous oxide. Examples of the catalyst for decomposing the nitrous oxide, which can be used, include an alumina-type catalyst where a noble metal is supported on alumina. At least one of the catalysts selected from the group consisting of the following (I) to (III) can be used:

(I) a catalyst where aluminium, magnesium and rhodium are supported on a support;
(II) a catalyst where magnesium and rhodium are supported on an alumina support; and
(III) a catalyst where rhodium is supported on a support in which a spinel crystalline complex oxide is formed by magnesium and at least a part of aluminum.

Moreover, at least one of the catalysts selected from the group consisting of the following (IV) to (VI) can be used:

(IV) a catalyst comprising a support having supported thereon aluminum, rhodium and at least one metal selected from the group of zinc, iron and manganese.
(V) a catalyst comprising an alumina support having supported thereon rhodium and at least one metal selected from the group of zinc, iron and manganese.
(VI) a catalyst comprising a support having supported thereon rhodium, the support having therein a spinel crystalline complex oxide formed by at least a part of aluminum and at least one metal selected from the group of zinc, iron and manganese.

At the time of decomposing the nitrous oxide, NOx in excess of the allowable concentration may be generated. In such a case, in order to reduce the amount of NOx to 1 ppm or less, it is preferable to use at least one catalyst for decomposing the nitrous oxide selected from the above (I) to (VI).

The temperature of the decomposition reactor filled with the nitrous oxide decomposition catalyst can be set in the range from 200 to 600° C. and is preferably from 300 to 500° C., more preferably from 350 to 450° C. By setting the temperature of the decomposition reactor filled with the catalyst to this temperature range, nitrous oxide can be efficiently decomposed and at the same time, by using the above-described decomposition catalyst, the amount of NOx generated can be reduced to 1 ppm or less. If the temperature of the decomposition reactor is less than 200° C., nitrous oxide cannot be sufficiently decomposed, whereas if the temperature exceeds 600° C., the catalyst life is shortened and also in view of the safety, use of such a high temperature in excess of 600° C. in facilities of a hospital is not preferred.

Nitrous oxide is contained in the waste anesthetic gas in a concentration of 3 to 70%. The waste anesthetic gas discharged from the waste anesthetic gas removing apparatus where the volatile anesthetic is adsorbed and thereby removed, is successively introduced into a nitrous oxide decomposition reactor. The gas introduced here is accompanied and diluted by a compressed air, nevertheless, the concentration of the nitrous oxide contained therein is sometimes as high as around 25%. From the aspect of the decomposition capacity of the catalyst, there arises no problem even if the gas is introduced as it is into the catalyst layer. However, on considering the activity and the life of the catalyst, the concentration of the nitrous oxide introduced into the catalyst layer is preferably lower. Accordingly, the gas introduced into the nitrous oxide decomposition reactor is preferably diluted to reduce the nitrous oxide concentration to 10% or less, more preferably 5% or less.

The gas for diluting the gas containing nitrous oxide is not particularly limited as long as the gas does not affect the catalyst, and for example, air, nitrogen or inert gas such as helium and argon may be used. From the economical viewpoint, dry air or atmospheric air is preferably used as it is.

The temperature of the gas introduced into the nitrous oxide decomposition reactor is nearly a normal temperature and the gas decomposed by the catalyst is heated to 200 to 600° C. In the treating process of the present invention, both before and after the introduction into the decomposition reactor, the gas is passed through a heat exchanger disposed at the inlet and the outlet of the decomposition reactor to perform heat exchange between the gas introduced into the reactor and the gas discharged from the reactor, so that the heating energy and cooling energy can be reduced and the energy efficiency can be elevated.

In the treating process of the present invention, the concentration of the nitrous oxide gas is detected before the decomposed gas discharged from the decomposition reactor is released into atmosphere so that the reaction temperature of the decomposition reactor can be controlled based on the detected concentration. The nitrous oxide discharged from the decomposition reactor outlet is monitored to detect the reduction in the activity of the nitrous oxide decomposition catalyst, and depending on the detected nitrous oxide concentration, the decomposition reaction temperature is controlled, for example, by raising the temperature.

In another embodiment, the process for treating a waste anesthetic gas of the present invention is characterized in that (1) a step of introducing a waste anesthetic gas containing a volatile anesthetic and nitrous oxide into at least one of adsorbing cylinders connected in parallel and contacting the gas with an adsorbent filled in the adsorbing cylinder, thereby adsorption-removing the volatile anesthetic contained in the waste anesthetic gas, is first performed, (2) a step of contacting the gas containing nitrous oxide discharged from the step (1) with a catalyst, thereby decomposing the nitrous oxide is then performed, and (3) a step of desorbing the volatile anesthetic from the adsorbent having adsorbed the volatile anesthetic to regenerate the adsorbent, cooling the desorbed volatile anesthetic, and recovering the liquefied or frozen volatile anesthetic, is finally performed.

The step (1) of adsorption-removing the volatile anesthetic and the step (3) of desorbing the volatile anesthetic are preferably performed at the same time by changing over the adsorbing cylinders connected in parallel alternately to the step (1) and to the step (3). In the step (3), the adsorbent having adsorbed a volatile anesthetic is decompressed by a vacuum pump to desorb the adsorbed volatile anesthetic, whereby the adsorbent can be regenerated. That is, the desorption and recovery of the volatile anesthetic from the adsorbent means at the same time the regeneration of the adsorbent. The adsorbent after the volatile anesthetic is desorbed can be re-used again as an adsorbent for removing a volatile anesthetic from a waste anesthetic gas. Accordingly, when the adsorbing cylinders are operated by changing the gas flow to a new adsorbing cylinder during the regeneration of the adsorbent, the regeneration of the adsorbent and the recovery of the desorbed volatile anesthetic can be performed almost at the same time without stopping the operation of the treating apparatus. The change to respective steps can be performed, for example, by controlling an electromagnetic valve using a sequencer.

In the step (3), at the time of decompressing the adsorbing cylinder filled with an adsorbent by a vacuum pump, a purge gas may be introduced into the adsorbing cylinder, so as to desorb the adsorbed volatile anesthetic, whereby the adsorbent can be regenerated. The purge gas is not particularly limited but, for example, air, nitrogen and inert gas can be used. From the economical viewpoint, dry air or atmospheric air is preferably used as it is.

In the present invention, at the same time with the regeneration of the adsorbent by desorbing the volatile anesthetic adsorbed to the adsorbent from the adsorbent, the desorbed volatile anesthetic is introduced into a cooling apparatus and thereby the volatile anesthetic can be liquefied or frozen and then recovered. The recovered volatile anesthetic may be purified again or may be decomposed by incineration or by contacting it with a decomposing agent.

The volatile anesthetic desorbed from the adsorbent and introduced into the cooling apparatus is mostly liquefied or frozen, however, the gas discharged from the cooling apparatus contains a volatile anesthetic corresponding almost to a vapor pressure at the cooling temperature. This is a very slight amount, but by introducing the gas discharged from the cooling apparatus into at least one of adsorbing cylinders connected in parallel and contacting the gas with an adsorbent filled in the adsorbing cylinder, the gas discharged from the cooling apparatus can be made to contain substantially no residual volatile anesthetic. Furthermore, as described above, for desorbing the volatile anesthetic from the adsorbent and thereby regenerating the adsorbent, a purge gas can be used and also in this case, by cooling the gas containing the volatile anesthetic and introducing the gas after the volatile anesthetic is liquefied or frozen and then recovered, into at least one adsorbing cylinders connected in parallel to contact the gas with the adsorbent filled in the adsorbing cylinder, the discharged gas can be made to contain substantially no residual volatile anesthetic.

When the gas containing the nitrous oxide after adsorption-removing the volatile anesthetic is made contact to a catalyst for decomposing nitrous oxide, the gas may be introduced to a guard adsorbing cylinder filled with the adsorbent described above. Using the guard adsorbing cylinder can prevent the volatile anesthetic from flowing into a catalyst for decomposing nitrous oxide even when the adsorbing cylinder loses its adsorbing capacity. The number and capacity of the guard cylinders are not specifically limited and can be selected depending on operational conditions.

The temperature for cooling the volatile anesthetic desorbed from the adsorbent may be from −95 to 10° C. but is preferably from −90 to 5° C., more preferably from −40 to 5° C. and most preferable from −20 to 5° C. As the cooling temperature is as low as possible, the efficiency in recovering the volatile anesthetic is improved, therefore, for example, the cooling may be performed by lowering the temperature to the freezing point of the volatile anesthetic, however, in view of the capacity of refrigerator or the heat loss, the temperature is preferably at least 10° C. or less.

In the case where the gas containing the desorbed volatile anesthetic contains moisture, the gas may be dehydrated by cooling or by using an adsorbent before cooling the volatile anesthetic. Controlling the cooling temperature of the volatile anesthetic in the range described above enables recovering both of the volatile anesthetic and moisture. As described above, a vapor pressure portion of the volatile anesthetic not recovered at the cooling temperature can be almost completely adsorbed and removed, for example, by again contacting the portion together with a purge gas with an adsorbent.

If the volatile anesthetic is not previously treated with an adsorbent but removed only by cooling, in the case of using sevoflurane (fluoromethyl 2,2,2-trifluoro-1-(trifluoromethyl)ethyl ether) as a volatile anesthetic, sevoflurane remains in the gas even after cooling to −90° C., in a concentration of about 100 ppm. Although the instantaneous value is very small, if the gas containing the residual volatile anesthetic is reacted with a nitrous oxide decomposition catalyst for a long time, the residual volatile anesthetic disadvantageously gives rise to the reduction in the activity of the catalyst. According to the process for treating a waste anesthetic gas of the present invention, the volatile anesthetic can be removed by the adsorption and therefore, the cooling temperature needs not be lowered to the cryogenic point less than −95° C. As such, the process for treating a waste anesthetic gas of the present invention is advantageous also in view of the profitability.

The method for cooling the volatile anesthetic is not particularly limited and for example, a cooling method with dry ice or liquid nitrogen using a denatured alcohol as a refrigerant may be employed. In view of easy handleability, a two refrigerant cooler or an exclusive cryogenic cooler may be used.

The apparatus for treating a waste anesthetic gas of the present invention is described below.

The apparatus for treating a waste anesthetic gas of the present invention is an apparatus for treating a waste anesthetic gas containing a volatile anesthetic and nitrous oxide and characterized by comprising an adsorbing cylinder filled with an adsorbent for adsorbing a volatile anesthetic, a decompression unit for desorbing the adsorbed volatile anesthetic from the adsorbent and regenerating the adsorbent, a cooler for cooling or freezing the desorbed volatile anesthetic, a recovery unit for recovering the cooled or frozen volatile anesthetic, and a decomposition reactor filled with a catalyst for decomposing the nitrous oxide contained in the waste anesthetic gas.

The adsorbing cylinder filled with an adsorbent for adsorbing the volatile anesthetic is connected with the decomposition reactor filled with a catalyst for decomposing the nitrous oxide such that the waste anesthetic gas is first introduced into the adsorbing cylinder and then the gas discharged from the adsorbing cylinder containing the nitrous oxide is introduced into the decomposition reactor filled with a catalyst for decomposing nitrous oxide. Furthermore, one or a plurality of adsorbing cylinders each filled with an adsorbent for adsorbing the volatile anesthetic are provided and, in the case that a plurality of adsorbing cylinders are used, they are preferably connected in parallel and the gas flow can be changed so that an arbitrary adsorbing cylinder can be used in changing over operation.

BEST MODE FOR CARRYING OUT THE INVENTION

The apparatus for treating a waste anesthetic gas of the present invention is described below by referring to the drawings.

FIG. 1 is a view showing one example of the apparatus for treating a waste anesthetic gas of the present invention, where from the waste anesthetic gas containing a volatile anesthetic and nitrous oxide discharged from an operating room, the volatile anesthetic is removed by adsorption and then recovered and successively, nitrous oxide is decomposed. The apparatus for treating a waste anesthetic gas shown in FIG. 1 is fundamentally constructed by a device for use in the step of treating a waste anesthetic gas, comprising an adsorbing cylinder 1 filled with an adsorbent for adsorbing and thereby removing the volatile anesthetic, a nitrous oxide decomposition reactor 3 filled with a nitrous oxide decomposition catalyst, a heat exchanger 14, a diluting gas-inducing pump 5 for diluting the gas containing nitrous oxide, a flow meter 4, a diluting gas inlet 6 and a nitrous oxide gas detector 7 for measuring the concentration of the nitrous oxide in the discharged gas after the decomposition of the nitrous oxide; and a device for use in the step of desorbing and recovering the volatile anesthetic adsorbed to the adsorbent and at the same time regenerating the adsorbent, comprising a cryogenic refrigerator 9, a cooler 2 for cooling the volatile anesthetic, a recovery unit 8 for recovering the cooled volatile anesthetic and a vacuum pump 10.

In the waste anesthetic gas treating apparatus of FIG. 1, one adsorbing cylinders for adsorbing the volatile anesthetic is provided. The waste anesthetic gas is introduced to adsorbing cylinder 1 via valve V6, and then into a nitrous oxide decomposition reactor 3 via valve V7. The time for adsorption treatment can be determined according to the adsorbing capacity of the adsorbent. As described above, it is desirable to stop the treatment at a stage where the adsorption by the adsorbent reaches about ¾ of the adsorbing capacity of the adsorbent so as to adsorb the volatile anesthetic efficiently.

As a process for recovering the volatile anesthetic adsorbed to the adsorbent, a process may be performed after closing valve V6 to stop the supply of the waste anesthetic gas, for example, by closing valve V7, desorbing the volatile anesthetic using a vacuum pump while introducing a diluting gas via valve V3, and introducing the desorbed volatile anesthetic to cooler 2 and to a recovery unit 8 for recovering the volatile anesthetic. The regenerated adsorbent after desorbing the volatile anesthetic can be used repeatedly. The waste anesthetic gas treatment can start again by closing valves V2 and V3 and opening valves V6 and V7.

Figure 2:
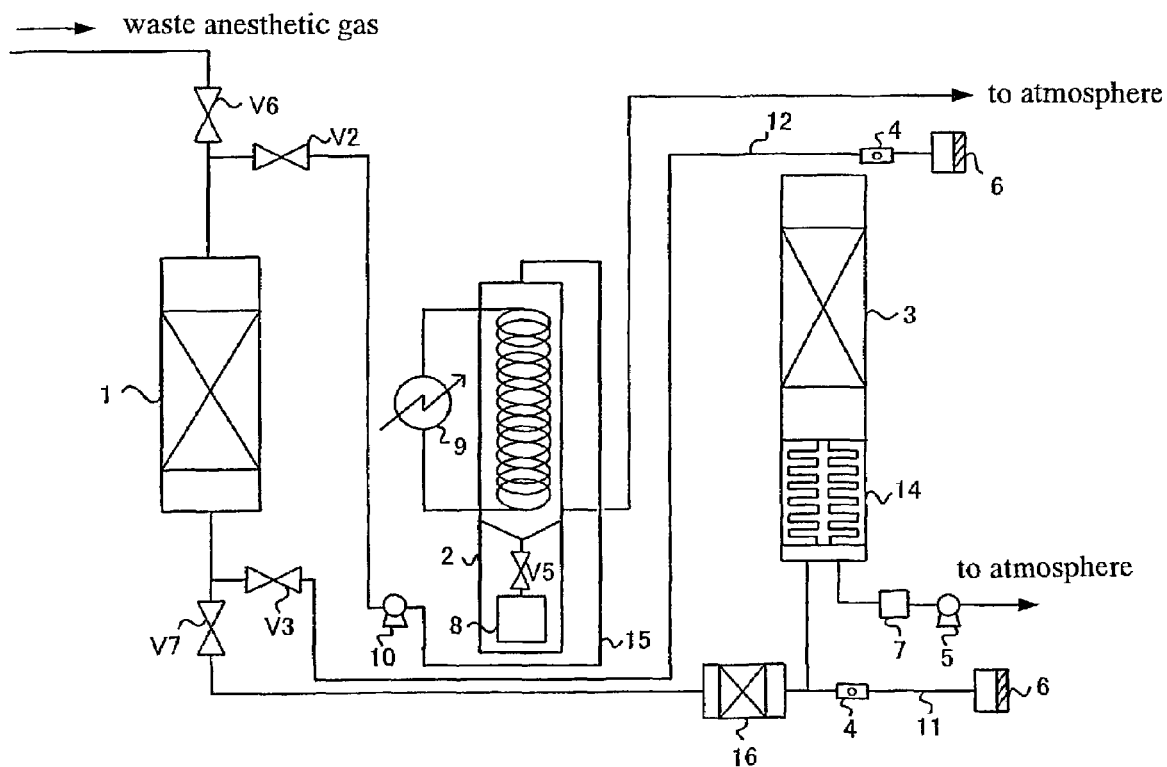
FIG. 2 is a schematic view showing one example of the apparatus for treating a waste anesthetic gas of the present invention.

FIG. 2 shows another example of the waste anesthetic gas treating apparatus of the present invention, and in this apparatus a guard adsorbing cylinder 16 is added to the waste anesthetic gas treating apparatus in FIG. 1. The position to insert the guard adsorbing cylinder 16 provided for the case that the adsorbing cylinder loses the adsorbing capability is not specifically limited as long as it is located between the adsorbing cylinder 1 and the nitrous oxide decomposition reactor 3.

Figure 3:
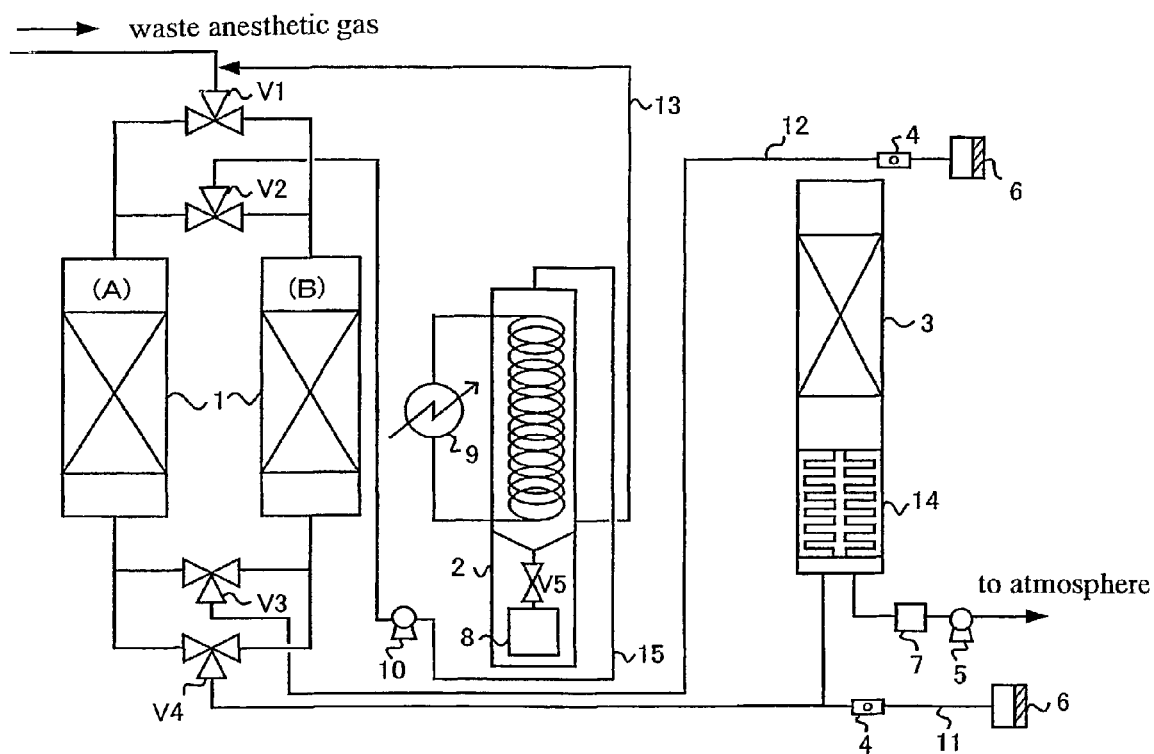
FIG. 3 is a schematic view showing one example of the apparatus for treating a waste anesthetic gas of the present invention.

FIG. 3 shows another example of the waste anesthetic gas treating apparatus of the present invention. The waste anesthetic gas treating apparatus in FIG. 3 fundamentally consists of a device for use in the step of treating a waste anesthetic gas, comprising two cylinders 1 filled with an adsorbent to adsorb-remove the volatile anesthetic, a nitrous oxide decomposition reactor 3 filled with a nitrous oxide decomposition catalyst, a heat exchanger 14, a diluting gas-inducing pump 5 for diluting the gas containing nitrous oxide, a flow meter 4, a diluting gas inlet 6 and a nitrous oxide gas detector 7 for measuring the concentration of the nitrous oxide in the discharged gas after the decomposition of the nitrous oxide; and a device for use in the step of desorbing and recovering the volatile anesthetic adsorbed to the adsorbent and at the same time regenerating the adsorbent, comprising a cryogenic refrigerator 9, a cooler 2 for cooling the volatile anesthetic, a recovery unit 8 for recovering the cooled volatile anesthetic and a vacuum pump 10.

In the waste anesthetic gas treating apparatus of FIG. 3, two adsorbing cylinders (A) and (B) for adsorbing the volatile anesthetic are provided and connected in parallel. The changeover between the adsorbing cylinder (A) and the adsorbing cylinder (B) can be performed by a valve V1 and the treating apparatus can be continuously operated, for example, by performing the desorption and recovery of the volatile anesthetic to regenerate the adsorbent in the adsorbing cylinder (B) while the adsorbing cylinder (A) is performing the adsorption operation.

The adsorbent filled in the adsorbing cylinder can be selected according to the kind of the volatile anesthetic contained in the waste anesthetic gas. Out of two routes (A) and (B) of the adsorbing cylinder 1, the waste anesthetic gas is introduced into the adsorbing cylinder (A), for example, from the side (A) of the valve V1 by controlling the valves V1 to V4 and the volatile anesthetic is first adsorbed and thereby removed. The gas from which the volatile anesthetic is removed by adsorption in the adsorbing cylinder (A) is introduced into the decomposition reactor 3 filled with a nitrous oxide decomposition catalyst through the valve V4. During this, the side (B) of the valve V1 and the side (B) of the valve V4 are closed.

The decomposition reactor 3 can be heated, for example, by an electric heater. The catalyst filled in the decomposition reactor 3 may be selected from the above examples, such as an alumina-type catalyst where a noble metal is supported on alumina, a catalyst where magnesium and rhodium are supported on an alumina support. The nitrous oxide-containing gas introduced into the decomposition reactor 3 can be diluted by taking in an atmospheric air from the diluting gas inlet 6 using the diluting gas-inducing pump 5 while controlling the flow rate by the flow meter 4.

The valves V1 and V4 work for the changeover of the line in the waste anesthetic gas treating step having two routes of the adsorbing cylinders (A) and (B), and the valves V2 and V3 work for the step of desorbing the volatile anesthetic from the adsorbing cylinder and regenerating the adsorbent. By previously determining the treating capacity of the adsorbent in adsorbing the volatile anesthetic and by controlling the valves V1 and V4 after the passing of a predetermined time according to the amount of the gas treated, the line can be automatically changed to the adsorbing cylinder (B) as the second route. When the adsorption step line is changed to the side (B), preferably at the same time therewith, the adsorbing cylinder (A) having adsorbed thereto the volatile anesthetic can be connected to the vacuum pump 10 by adjusting the valves V2 and V3.

By opening the side (A) of the valve V2 and closing the valve V3, the adsorbing cylinder (A) is decompressed by the vacuum pump 10 and the desorbed volatile anesthetic is introduced into the cooler 2 through the pipeline 15. The volatile anesthetic is cooled in the cooler 2, thereby liquefied or frozen and then recovered using the recovery unit 8. At the time of decompressing the adsorbing cylinder (A) by means of the vacuum pump 10, a purge gas may be used. In the case of using a purge gas, an atmospheric air taken in from the diluting gas inlet 6 is introduced into the adsorbing cylinder (A) through the diluting gas inlet line 12 and the amount introduced can be controlled by adjusting the valves V2 and V3.

The recovery unit 8 is equipped with an open-close valve V5. Here, the treating apparatus of the present invention comprises, as shown in FIG. 3, an unrecovered gas recovering line 13 so as to adsorb and thereby remove the unrecovered volatile anesthetic corresponding to the vapor pressure at the cooling temperature. The vapor pressure portion of the volatile anesthetic can be returned to the front of the valve V1 through the unrecovered gas recovering line 13 and again contacted with the adsorbent.

In the decomposition reactor 3, nitrous oxide is decomposed into nitrogen and oxygen and then discharged. The discharged gas is heat-exchanged with the gas introduced into the decomposition reactor 3 in the heat exchanger 14 and then released into atmosphere through the nitrous oxide gas detector 7. At this time, the nitrous oxide concentration can be detected by the nitrous oxide gas detector 7 to control the reaction temperature in the decomposition reactor 3. By constructing the decomposition reactor 3 self-containing the above-described nitrous oxide decomposition catalyst and the heat exchanger 14 into a monolithic structure and designing this as a vertical unit which is disposed vertically, downsizing of the apparatus and reduction in the heat loss can be achieved.

Figure 4:
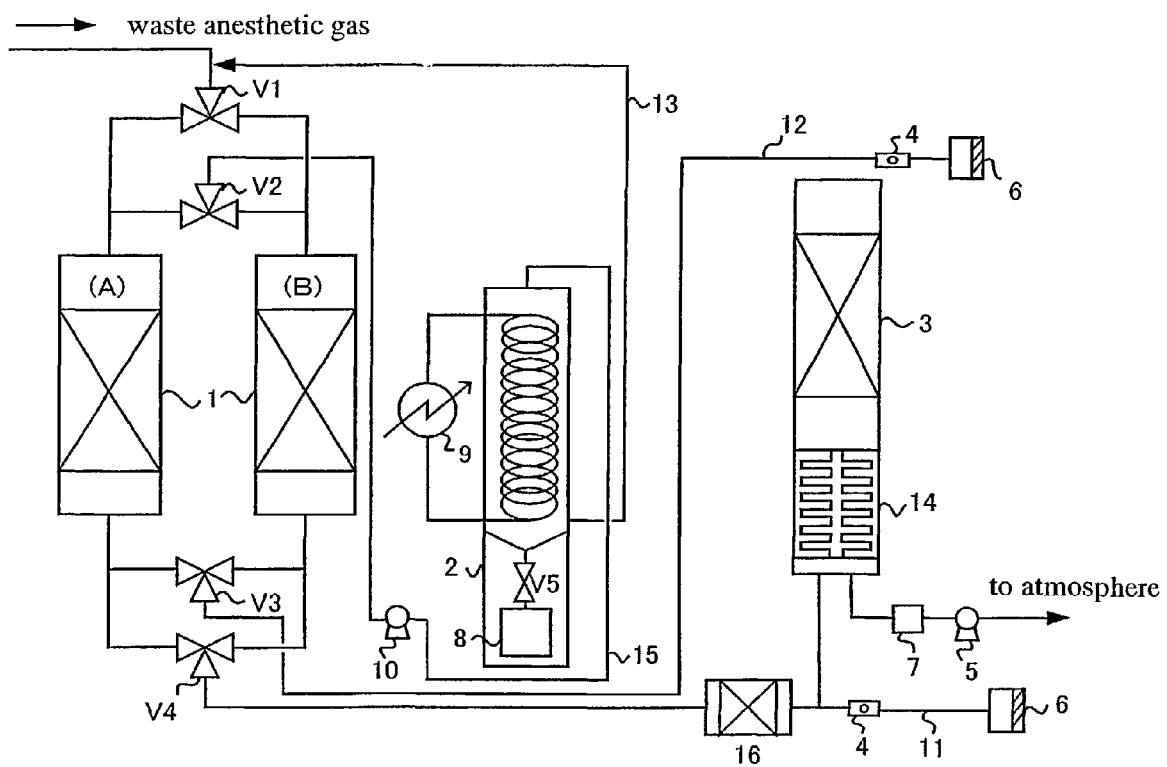
FIG. 4 is a schematic view showing one example of the apparatus for treating a waste anesthetic gas of the present invention.

FIG. 4 shows another example of the waste anesthetic gas treating apparatus of the present invention, and in this apparatus a guard adsorbing cylinder 16 is added to the waste anesthetic gas treating apparatus in FIG. 3. The position to insert the guard adsorbing cylinder 16 provided for the case that a adsorbing cylinder loses the adsorbing capability is not specifically limited as long as it is located between the adsorbing cylinder 1 and the nitrous oxide decomposition reactor 3. The apparatus in FIG. 3 is provided with two adsorbing cylinders in parallel, which enables a stabilized operation for a long time by switching to another cylinder before one cylinder loses its adsorbing capacity. Installing the guard adsorbing cylinder 16 enables further safer operation.

INDUSTRIAL APPLICABILITY

When the process and the apparatus for treating a waste anesthetic gas of the present invention are used, the volatile anesthetic contained in a waste anesthetic gas discharged from an operating room of a hospital by a waste anesthetic gas removing apparatus can be adsorbed to an adsorbent and thereby removed, and successively the nitrous oxide can be decomposed into nitrogen and oxygen. By using the process and the apparatus for treating a waste anesthetic gas of the present invention, a volatile anesthetic having a possibility of destroying the ozone layer or nitrous oxide as a global warming gas, which are concerned in view of the global environmental protection, can be made harmless while preventing the release into atmosphere. Furthermore, the treating apparatus of the present invention is compact and therefore, can be installed on the roof of a hospital or in a hospital facility having a relatively small space, such as machine room or pipeline collecting space, moreover, the apparatus is economical since a large amount of waste anesthetic gas can be treated continuously.

The invention claimed is:

1. A process for treating a waste anesthetic gas containing a volatile anesthetic and nitrous oxide discharged from an operating room comprising steps of contacting the gas with an adsorbent, thereby adsorption-removing the volatile anesthetic contained in the waste anesthetic gas, and then contacting the gas containing nitrous oxide with a catalyst for decomposing the nitrous oxide, thereby decomposing the nitrous oxide, wherein the concentration of the nitrous oxide contained after the decomposition of the nitrous oxide is detected and the temperature at the decomposition of the nitrous oxide is controlled based on the detected concentration of nitrous oxide.

2. The process for treating a waste anesthetic gas as claimed in claim 1, wherein the treating comprises the following two steps:
(1) a step of introducing a waste anesthetic gas containing a volatile anesthetic and nitrous oxide discharged from an operating room into an adsorbing cylinder, and contacting the gas with an adsorbent filled in the adsorbing cylinder, thereby adsorption-removing the volatile anesthetic contained In the waste anesthetic gas, and
(2) a step of contacting the gas containing nitrous oxide discharged from the step (1) with a catalyst, thereby decomposing the nitrous oxide.

3. The process for treating a waste anesthetic gas as claimed in claim 1, wherein the treating comprises the following two steps:
(1) a step of introducing a waste anesthetic gas containing a volatile anesthetic and nitrous oxide discharged from an operating room into at least one of adsorbing cylinders connected in parallel, and contacting the gas with an adsorbent filled in the adsorbing cylinder, thereby adsorption-removing the volatile anesthetic contained in the waste anesthetic gas, and
(2) a step of contacting the gas containing nitrous oxide discharged from the step (1) with a catalyst, thereby decomposing the nitrous oxide.

4. The process for treating a waste anesthetic gas as claimed in claim 2 or 3, further comprising the following step (3):
(3) a step of desorbing the volatile anesthetic from the adsorbent having adsorbed the volatile anesthetic to regenerate the adsorbent, cooling the desorbed volatile anesthetic, and recovering the liquefied or frozen volatile anesthetic.

5. The process for treating a waste anesthetic gas as claimed in claim 4, wherein the step (1) and the step (3) are performed at the same time by changing over the adsorbing cylinders connected in parallel alternately to the step (1) and to the step (3).

6. The process for treating a waste anesthetic gas as claimed in claim 5, wherein the changeover between the step (1) and the step (3) is performed under control by a sequencer.

7. The process for treating a waste anesthetic gas as claimed in claim 4, wherein the step (3) is performed under reduced pressure and the gas discharged from the step (3) is introduced into at least one of adsorbing cylinders connected in parallel and contacted with an adsorbent filled in the adsorbing cylinders to remove by adsorption the unrecovered volatile anesthetic contained in the gas discharged from the step (3).

8. The process for treating a waste anesthetic gas as claimed in claim 4, wherein the step (3) is performed under reduced pressure while introducing a purge gas and the gas discharged from the step (3) is introduced into at least one of adsorbing cylinders connected in parallel and contacted with an adsorbent filled in the adsorbing cylinder to remove by adsorption the unrecovered volatile anesthetic contained in the gas containing a purge gas discharged from the step (3).

9. The process for treating a waste anesthetic gas as claimed in claim 4, wherein in the step (3), the temperature at the cooling of the desorbed volatile anesthetic is from −95 to 10° C.

10. The process for treating a waste anesthetic gas as claimed in claim 1, wherein the concentration of the volatile anesthetic contained in the waste anesthetic gas is from 0.1 to 3%.

11. The process for treating a waste anesthetic gas as claimed in claim 1, wherein the volatile anesthetic is a fluoroether compound.

12. The process for treating a waste anesthetic gas as claimed in claim 1, wherein the volatile anesthetic is 2-bromo-2-chloro-1,1,1-trifluoro-ethane, 1-chloro-2,2,2-trifluoroethyl difluoromethyl ether and/or fluoromethyl-2,2,2-tiifiuoro-1-(trifluoromethyl) ethyl ether.

13. The process for treating a waste anesthetic gas as claimed in claim 1, wherein the adsorbent is at least one adsorbent selected from the group consisting of activated carbon, zeolite, silica, mesoporous silica and alumina.

14. The process for treating a waste anesthetic gas as claimed in claim 13, wherein the adsorbent has a pore size of 5 to 100 Å.

15. The process for treating a waste anesthetic gas as claimed in claim 1, wherein the concentration of the nitrous oxide contained in the waste anesthetic gas is from 3 to 70%.

16. The process for treating a waste anesthetic gas as claimed in claim 1, wherein the catalyst for decomposing the nitrous oxide is an alumina-type catalyst.

17. The process for treating a waste anesthetic gas as claimed in claim 1, wherein the catalyst for decomposing the nitrous oxide is at least one catalyst selected from the group consisting of the following catalysts (I) to (III):
   (I) a catalyst comprising a support having supported thereon aluminum, magnesium and rhodium,
   (II) a catalyst comprising an alumina support having supported thereon magnesium and rhodium, and
   (III) a catalyst comprising a support having supported thereon rhodium, the support having therein a spinel crystalline complex oxide formed by magnesium and at least a part of aluminum.

18. The process for treating a waste anesthetic gas as claimed in claim 1, wherein the catalyst for decomposing the nitrous oxide is at least one catalyst selected from the group consisting of the following catalysts (IV) to (VI):
   (IV) a catalyst comprising a support having supported thereon aluminum, rhodium and at least one metal selected from the group of zinc, iron and manganese.
   (V) a catalyst comprising an alumina support having supported thereon rhodium and at least one metal selected from the group of zinc, iron and manganese.
   (VI) a catalyst comprising a support having supported thereon rhodium, the support having therein a spinel crystalline complex oxide formed by at least a part of aluminum and at least one metal selected from the group of zinc, iron and manganese.

19. The process for treating a waste anesthetic gas as claimed in claim 1, wherein the temperature at the decomposition of the nitrous oxide is from 200 to 600° C.

20. The process for treating a waste anesthetic gas as claimed in any one of claims 17 to 19, wherein the amount of NOx generated at the decomposition of the nitrous oxide is 1 ppm or less.

21. The process for treating a waste anesthetic gas as claimed in claim 2 or 3, wherein in the step (2), heat exchange is performed between the gas discharged from the step (1) and the gas discharged from the step (2) after the decomposition of the nitrous oxide.

* * * * *